United States Patent
Varis

(10) Patent No.: US 6,702,146 B2
(45) Date of Patent: Mar. 9, 2004

(54) SYSTEM FOR DISPENSING PILL- OR CAPSULE-FORM MEDICATIONS IN DESIRED DOSES

(75) Inventor: Reijo Varis, Helsinki (FI)

(73) Assignee: Addoz Oy, Helsinki (FI)

( * ) Notice: Subject to any disclaimer, the term of this patent is extended or adjusted under 35 U.S.C. 154(b) by 0 days.

(21) Appl. No.: 10/369,924

(22) Filed: Feb. 19, 2003

(65) Prior Publication Data

US 2003/0127463 A1 Jul. 10, 2003

Related U.S. Application Data

(63) Continuation of application No. PCT/FI01/00751, filed on Aug. 28, 2001.

(30) Foreign Application Priority Data

Aug. 28, 2000 (FI) ............................................. 20001889

(51) Int. Cl.[7] ................................................ G07F 11/00
(52) U.S. Cl. ................................ 221/3; 221/9; 700/243
(58) Field of Search ............................. 221/2, 3, 7, 15, 221/9, 82, 83, 197, 266; 700/242, 243, 231, 237

(56) References Cited

U.S. PATENT DOCUMENTS

| | | |
|---|---|---|
| 4,674,651 A | 6/1987 | Scidmore et al. |
| 4,695,954 A | 9/1987 | Rose et al. |
| 4,768,176 A | 8/1988 | Kehr et al. |
| 4,785,969 A | 11/1988 | McLaughlin |
| 4,911,327 A | 3/1990 | Shepherd et al. |
| 5,372,276 A | 12/1994 | Daneshvar |
| 5,392,952 A | 2/1995 | Bowden |
| 5,490,610 A | 2/1996 | Pearson |
| 5,564,593 A | 10/1996 | East, Sr. |
| 5,710,551 A | 1/1998 | Ridgeway |
| 5,971,594 A | 10/1999 | Sahai et al. |
| 6,075,755 A | 6/2000 | Zarchan |
| 6,198,383 B1 | 3/2001 | Sekura et al. |
| 2001/0009398 A1 | 7/2001 | Sekura et al. |

FOREIGN PATENT DOCUMENTS

| | | |
|---|---|---|
| WO | WO 95/28142 | 10/1995 |
| WO | WO 9743999 | 11/1997 |
| WO | WO 99/43284 | 9/1999 |

*Primary Examiner*—Kenneth W. Noland
(74) *Attorney, Agent, or Firm*—Klauber & Jackson

(57) ABSTRACT

A system for dispensing pill- or capsule-form medications (61) in desired doses (60). The system comprises a dispensing device (35), which includes a cartridge (20, 40) rotatable relative to a housing or frame (10) and provided with discrete dosage compartments (27, 47) for desired doses of medication. The cartridge (20, 40) is manipulated by elements (18, 18a, 18b; 14a, 14b, 15, 18, 19), whereby each separate dosage compartment (27, 47) is rotatable relative to the housing or frame (10) to a dispensing point (4, 12) for the dose of medication (60). A signalling device (75, 76) producing a sound and/or light signal activates at preprogrammed times. An electronics unit (19, 55) containing a dispensing program is reprogrammable by means of an external programming device (36, 66, 101, 102). The cartridge (20, 40) is adapted to be disengaged from the dispensing device (35) and to be transferred to a loading device (80), which fills the dosage compartments (27, 47) of the cartridge with desired doses of medication and furnishes the filled cartridge with identification data (ID), on the basis of which the filled cartridge (20, 40) can be certifiably returned to the proper dispensing device (35), which is arranged to upkeep a dispensing event log at a distant control file (64a).

23 Claims, 8 Drawing Sheets

SYSTEM FOR DISPENSING PILL- OR CAPSULE-FORM MEDICATIONS IN DESIRED DOSES

This is a continuation of application No. PCT/FI01/00751 filed Aug. 28, 2001.

The invention relates to a system for dispensing pill- or capsule-form medications in desired doses, said system comprising a dispensing device which includes a housing or frame, a cartridge movable with respect to the housing or frame and provided with individual dosage compartments for desired doses of medication, means for manipulating the cartridge, whereby each individual dosage compartment is movable relative to the housing or frame to a dispensing point for the dose of medication, a signaling device giving a sound and/or light signal, which activates at preprogrammed points of time, and an electronics unit containing a dispensing program.

The invention relates also to a method for filling the dosage compartments of a cartridge of the above described type with a desired dose of medication.

Patent publication U.S. Pat. No. 5,805,051 discloses a medication dispenser device, which is provided with a clock and a sound signal means for reminding of the taking of medication at pre-programmed times. The cover of a medication container can be opened by the pressing of a button at appropriate times for medication, which are programmable in a versatile manner. The dispensing container is an ordinary compartment tray, from which the medicine taker must be able to choose a proper compartment and ingest the dose of medication contained therein. This type of dispensing is not suitable for patients whose mental ability has impaired, e.g. as a result of dementia. Filling the dispensing compartments with proper doses of medication is a tedious and high-precision operation, which is a burden to health care personnel as there are large numbers of patients both in hospitals and home care who must be provided with regular medication.

Patent publication U.S. Pat. No. 3,815,780 discloses a dispenser for medications, the dispensing being effected from a rotatable medication cartridge at regular intervals under the control of a clock in such a manner that each dose of medication can only be consumed during a preset time period, which is reminded of by means of an audible alarm. In addition, a visual signal can be used to indicate whether the medication can be taken, whether it has been taken, or whether it has not been taken at a prescribed time. The medications are released from the outer periphery of the cartridge by the action of gravity. The filling and handling of such a dispensing cartridge outside the device is awkward, nor is the dispensing cartridge intended to be disengaged. The dispensing cartridge is not suitable for refilling effected in an automated dispenser device. The programming of operation and limiting of a prescribed time interval are performed with a complicated mechanical assembly, which restricts programming possibilities substantially.

Patent publication U.S. Pat. No. 5,176,285 discloses an automatic pill dispensing apparatus having a plurality of medication cartridges mounted on a rotatable shaft within a housing or cabinet. The dosage compartments are included in a rotatable inner cartridge unit which is fitted in a cylindrical non-rotatable cartridge housing which seals the circumferential surface and one of the lateral surfaces of medication compartments. The cartridge includes also a disc-shaped template provided with an array of holes for selecting the timing of dosage dispension. A clock and a microprocessor are used to control drive motors for the apparatus and a dispense bar motor, which can be actuated with a push button at preprogrammed dispensing times. The filling and handling of this type of dosage cartridge outside the apparatus is awkward. The dosage cartridge is not suitable for refilling effected in an automated dispensing apparatus. The design is complicated and expensive and requires a multitude of various templates.

Patent publication U.S. Pat. No. 4,785,969 shows a medication dispensing system for controlled preprogrammed dispensing of medication to a patient and for creating a retrievable patient medication record. Manually rotatable carousel or magazine is adopted to receive individual cassettes of medicine. The cassettes have been manually preloaded in a preprogrammed manner in the hospital pharmacy or the like. The dispensing unit is programmed according to individual patient needs to signal at selected times when medication is prescribed. The medication can be accessed for dispensing only after entry of valid nurse or other personnel identification code into a dispensing unit memory. The dispensing unit further includes sensors for detecting removal of any medication cassette and for signalling the dispensing unit memory to create a corresponding patient medication record. A data transmission device is provided for selectively programming the dispensing unit memory and/or for reading the patient medication record from the memory. There is no real time dispensing event log at hand at any other place but in the dispensing device itself. The cassette system and loading of cassettes is difficult to control.

It is an object of the invention to provide a dispensing system for doses of medication, which is void of the above-mentioned drawbacks and shortcomings.

One specific object of the present invention is to keep a real time dispensing event log at a distant control location (such as in operator's internet server) which can be accessed via internet by those who have a key code or password.

According to a further object of the present invention said distant control location has programmable intelligence to follow dispensing schedule of each identified dispensing apparatus programmed to be followed and to give an alarm to one or more predetermined care giver via any appropriate communication path. This arrangement focuses the personal care to such patients who really need it. A greater number of patients can be followed and helped.

Still another object of the invention is to use a dispensing cartridge which facilitates filling or loading of the dosage compartments by doses of medication either manually or more or less in an automated manner by using a loading robotics, and which dispensing cartridge alone can also be used as a simple manually operated dispensing apparatus which is provided by visual indication of dispensing schedule, said visual indication serving both for manual filling or loading and for manually operated dispensing if the cartridge is used alone as a manually operated dispensing apparatus.

Still a further object of the invention is to provide, as a preferred option, a possibility to fill or load the dosage compartments of the dispensing cartridge under control of a computer program which gives an alarm if there are non-compatible medications to be loaded.

Still a further object of the invention is to provide a medication dispensing system wherein the information of identification, medication and dispensing schedule follows the cartridge and can be easily re-programmed and transferred between the cartridge and the memory of the dispensing device containing the dispensing program, as well as between either of these and a programming computer.

This and other objects are achieved according to the invention on the basis of the characterizing features set forth in the annexed claim 1. The non-independent claims disclose preferred embodiments of the invention, which facilitate dosing or loading logistics, offer versatile re-programming possibilities for dispensing, and facilitate the supervision of medication.

A few preferred embodiments of the present invention will now be described in more detail with reference made to the accompanying drawings, in which:

FIG. 10 shows a programming device useful between the dispensing device and a facility computer in hospital, rest home or the like.

Figure 1:
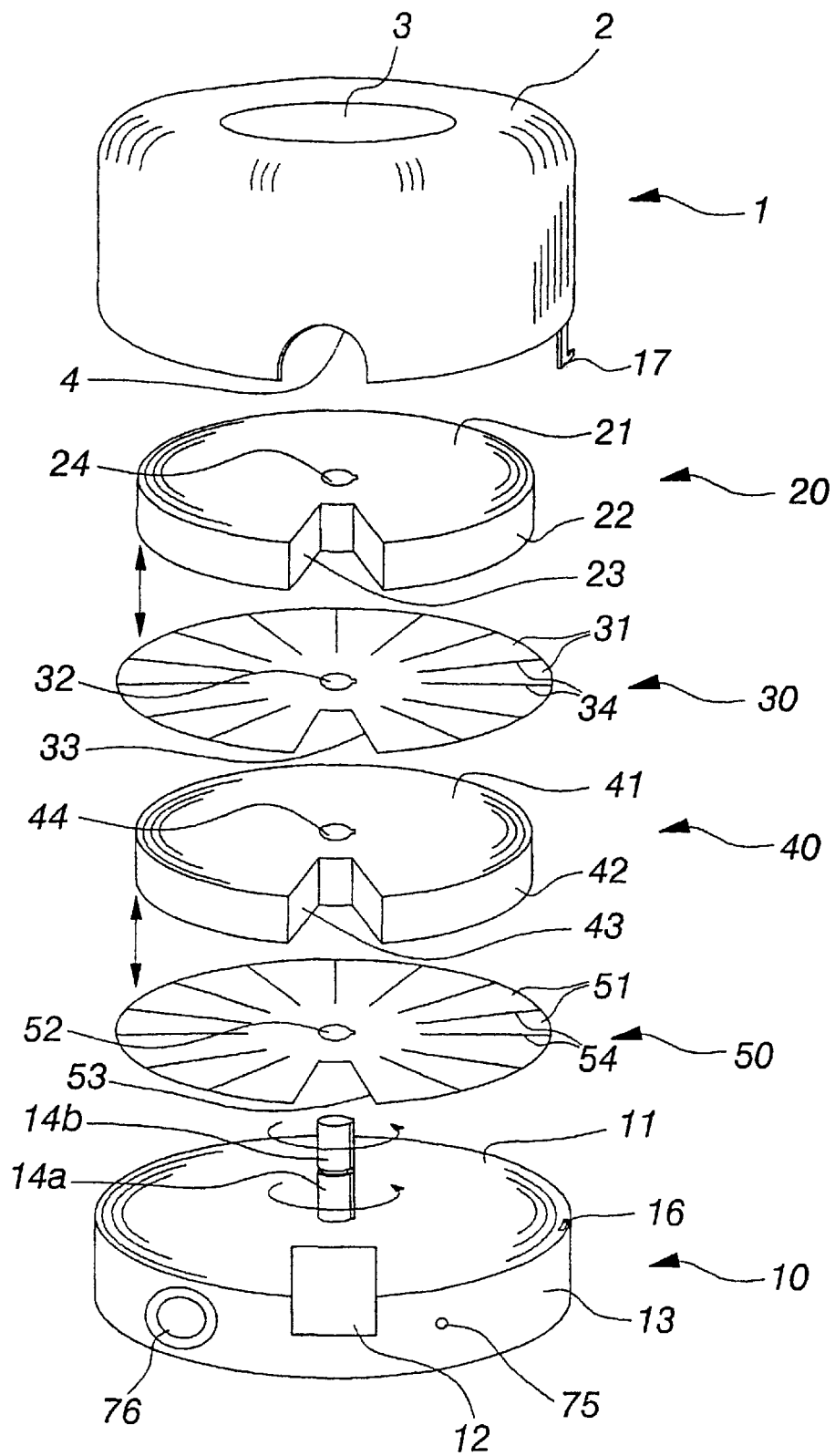
FIG. 1 shows schematically a segmented medication dispenser useful as part of a system of the invention.

Reference is first made to one embodiment (FIGS. 1–4) of a dispensing device, which can be used as part of a system of the invention.

FIGS. 1–4 show schematically an exploded view as well as a cutaway assembly view of a medication dispenser for delivering pill- or capsule-form medications 61 in desired doses. The loading device is essentially made up by cartridges 20, 30 and 40, 50 to be set on top of a frame 10 and, preferably, on top of each other. Around the cartridges 20, 30 and 40, 50 is fitted a cover 1. The cover 1 and the frame 10 constitute housing elements for the device to enclose the piled-up cartridges 20, 30 and 40, 50 within a space 5 inside the cover 1.

The frame 10 is preferably designed as a substantially flat cylinder with a hollow interior. This hollow space is provided with a motor 18, the drive unit of which comprises preferably an accumulator 6, a battery, or the like, arranged within the same space. The motor 18 is adapted to drive a shaft 15 which extends upwards through the top of the frame 10 to a height that is equal to the height of at least two of the piled-up cartridges 20, 30 and 40, 50. The hollow space is also provided with a memory and a processor for driving the motor 18 as desired, as well as with other accommodated peripheral devices, such as an amplifier 76 and a signal light 75.

The cartridges 20, 30 and 40, 50 are adapted to rotatable along with members 14a, 14b of the shaft 15 as a result of the engagement between a spline formed on the members 14a, 14b and a hole 24, 44 and a slot 25, 45 formed in the middle of the cartridges 20, 30 and 40, 50. The base disc 30, 50 is also provided with a matching engagement hole 32, 52.

Figure 2:
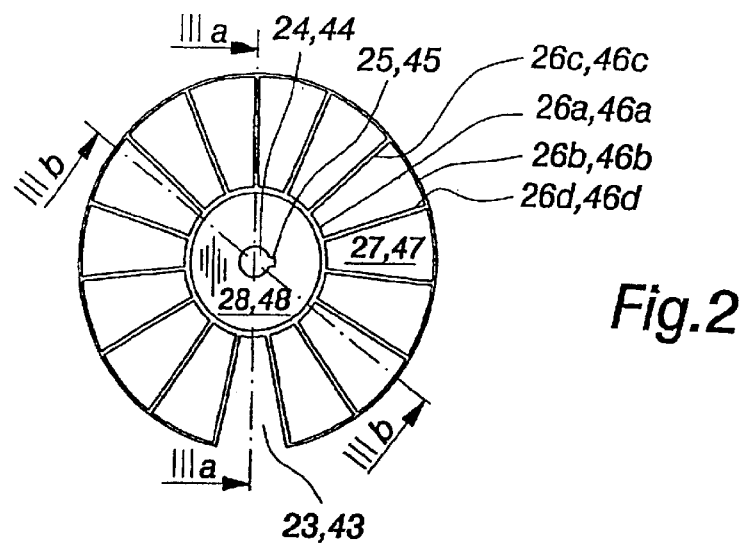
FIG. 2 shows schematically from below a dosage cartridge for the dispensing device of FIG. 1.
Figure 3A:
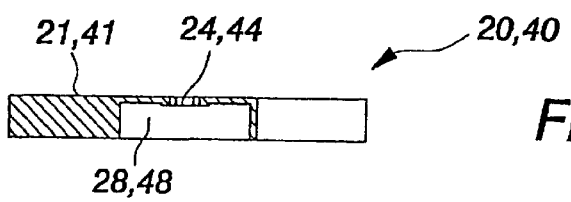
FIG. 3A shows schematically a sectional view along a line IIIa in FIG. 2.
Figure 3B:
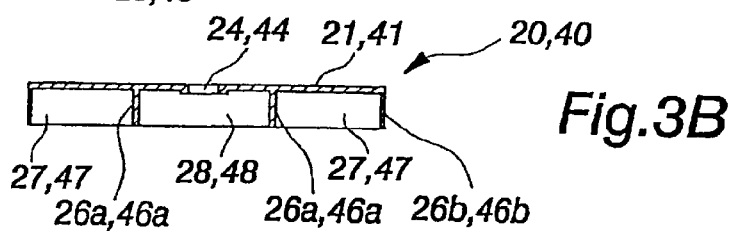
FIG. 3B shows schematically a sectional view along a line IIIb in FIG. 2.

The structure of a cartridge itself is shown schematically in FIGS. 2, 3A, 3B. Like the frame 10, the cartridge 20, 40 is also designed as a flat cylinder. The cartridge has its top surface 21, 41 provided with an annular outer rim 26b, 46b, extending downwards from the edge thereof and constituting a lateral face for the cartridge, as well as with an inner rim 26a, 46a which is radially about half the size of the outer rim. However, the inner rim has a radius which is preferably about ⅓–⅔ of that of the outer rim 26b, 46b. The annular space formed between these two rims is provided with partitions 26c, 26d, 46c, 46d extending radially from the outer rim 26b, 46b to the inner rim. Between those are defined separate segment-shaped (see FIG. 2) dosage compartments 27, 47. Each dosage compartment 27, 47 is loaded with a desired dose of medication 60 as described hereinafter.

The cartridge bottom is constituted by a separate circular base disc 30, 50, having a diameter which is slightly smaller than that of the frame 10 but somewhat larger than that of the cartridge 20, 40. The base disc 30, 50 is provided with elongated cuts or slits 34, 54 arranged radially inbound from its outer periphery. The cuts 34, 54 extend substantially as far away from the outer rim 26b, 46b of the cartridge 20, 40 as the inner rim 26a, 46a of the cartridge 20, 40.

In the assembled condition, the base disc 30, 50 has its cuts 34, 54 coinciding with the partitions 26c, 26d and 46c, 46d in the cartridge rotating direction. Between the cuts 34, 54 are defined segment-shaped flaps 31, 51 constituting the actual base disc 30, 50. The cartridges 20, 30 and 40, 50 are driven around the shaft 15 of the motor 18 through the intermediary of the separate shaft members 14a, 14b included in the shaft 15. These members are used for rotating individual cartridges 20, 30 and 40, 50 independently, regardless of each other. The rotary motion is preferably performed in such a way that the upper cartridge 20, 30 is first rotated a full circle, while the lower cartridge 40, 50 remains stationary. This is followed by rotating the lower cartridge 40, 50, while the upper cartridge remains stationary.

Both cartridges 20, 30 and 40, 50 are preferably provided with a recess 23, 33 and 43, 53 the size of a single dosage compartment 27, 47.

The cartridges 20, 30 and 40, 50 are preferably enclosed by means of a bowl-shaped cover 1 within a hollow space 5 provided therein. The cover 1 is secured to the frame 10 by means of a common. preferably latch-like locking mechanism 16, 17 mounted on the bottom edge of a shell portion 2 of the cover 1 and radially along the outer rim of the frame 10. The attachment between the cover 1 and the frame 10 may also be adapted to be secured by means of a key (not shown). The cover 1 has the top surface of its shell portion provided with bending elements 3, 7, 8a, 9a for the bottom flaps 31, 51. One of these elements is a dispenser press button 3. The dispenser press button 3 has its bottom edge provided with a rod 7 extending radially into the hollow space 5 towards a dispensing point 12. The rod 7 is adapted to be extensible downwards and towards the outer rims of the base discs 30, 50 of the cartridges 20, 30 and 40, 50. Adjacent to the base discs 30 and 50, preferably above the same, the rod 7 is provided with pushers 8a and 9a for bending the bottom flaps 31, 51 to a dispense position.

According to the exemplary embodiment, a single cartridge 20, 30 or 40, 50 includes 14 dosage compartments 27 or 47, i.e. two stacked-up cartridges 20, 30 and 40, 50 are provided with 28 dosage compartments. Thus, this represents a medication period of one week if the device is used for dispensing four doses of medication a day. Naturally, it is possible to vary the duration of a dispensing period as well as the number of dosage compartments 27, 47.

Figure 4:
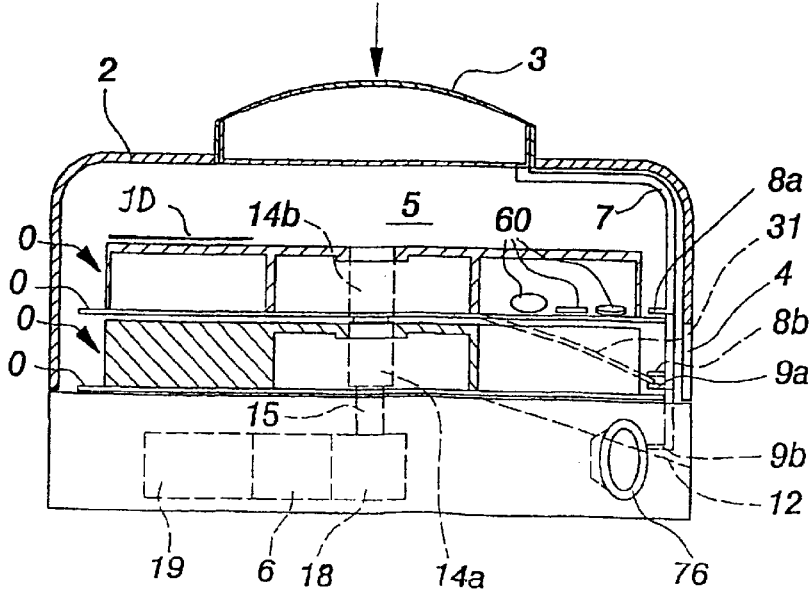
FIG. 4 shows schematically a sectional view of the medication dispenser of FIG. 1.

The cartridges 20, 30 and 40, 50 are installed in the device, such that the recess 23 and 43 included therein coincides with the dispensing point 12. Consequently, from the beginning halfway through a dispensing period (about 3,5 days) it is only the upper cartridge 20, 30 which rotates on the separate member 14b rotating through the intermediary of the motor 18 and the shaft 15. Thus, as the dispenser press button 3 is depressed, the pushers 8a, 9a carried by the rod 7 travel also across a distance to a position 8b, 9b, as shown in FIG. 4. At the same time, the pusher 8a presses the edge of the flap 31 closing the dosage compartment 27 coincident with the dispensing point 12 down into the recess 23 formed in the lower cartridge 40, 50, releasing a dose of medication 60 to the user by way of a dispensing outlet 4 provided in the vertical flank of the shell portion 2 of the cover 1. Halfway through the dispensing period, the upper cartridge 20, 30 has turned 360° and returned to its original position. From halfway through to the end of a dispensing period, it is only the lower cartridge which rotates on the separate member 14a rotating the cartridge 40, 50, the dose of medication 60 being released from the cartridge 40, 50 the same way as from the upper cartridge 20, 30.

Rotation of the cartridges 20, 30 and 40, 50 (separate shaft members 14a, 14b) is preferably controlled by means of a processor or logic 19 provided with a programmable memory. The program memory is pre-loaded with a basic program, which is capable of performing all necessary functions but which lacks information regarding desired functions and schedules therefor. An individual dispensing program for the doses 60 and/or parameters to be used by the basic program can be programmed into the program memory of the processor 19 from an external programming device, such as a PC or a mobile telephone, which can be manually fed with parameters regarding a dispensing schedule and desired audible signals, such as a number of reminders for medication, times therefor, and a person's name, which can be mentioned in conjunction with an sound signal reminder 76 produced by a voice synthesizer. Instead of a voice synthesizer, it is possible to use a separate mini cassette recorder, on whose magnetic tape the audible reminder signals can be dictated and which is controlled by the program through the intermediary of the processor 19. Of course, the use of a CD disk is also possible for outputting audible reminder signals. For example, the audible reminder signal may sound like "Mr. So-and-So, please take your daytime medication".

The signal light 75 blinks as long as the dose of medication 60 has been removed from the dosage compartment 27, 47 outside the device and made accessible to a user by pressing the dispensing button 3. If the dose 60 is not removed within a set period, after a few audible reminders, the program transfers the dose 60 away from the dispensing point 12, the dose 60 being no longer available during a dispensing period, e.g. a week, programmed in the device. The medication status can be checked by opening the cover 1. The cartridges 20, 40 are preferably made of transparent plastics. In more sophisticated equipment versions, it is of course possible to use also electronic monitoring, which records information about non-consumed medications and, if necessary, sets off an alarm.

Figure 5:
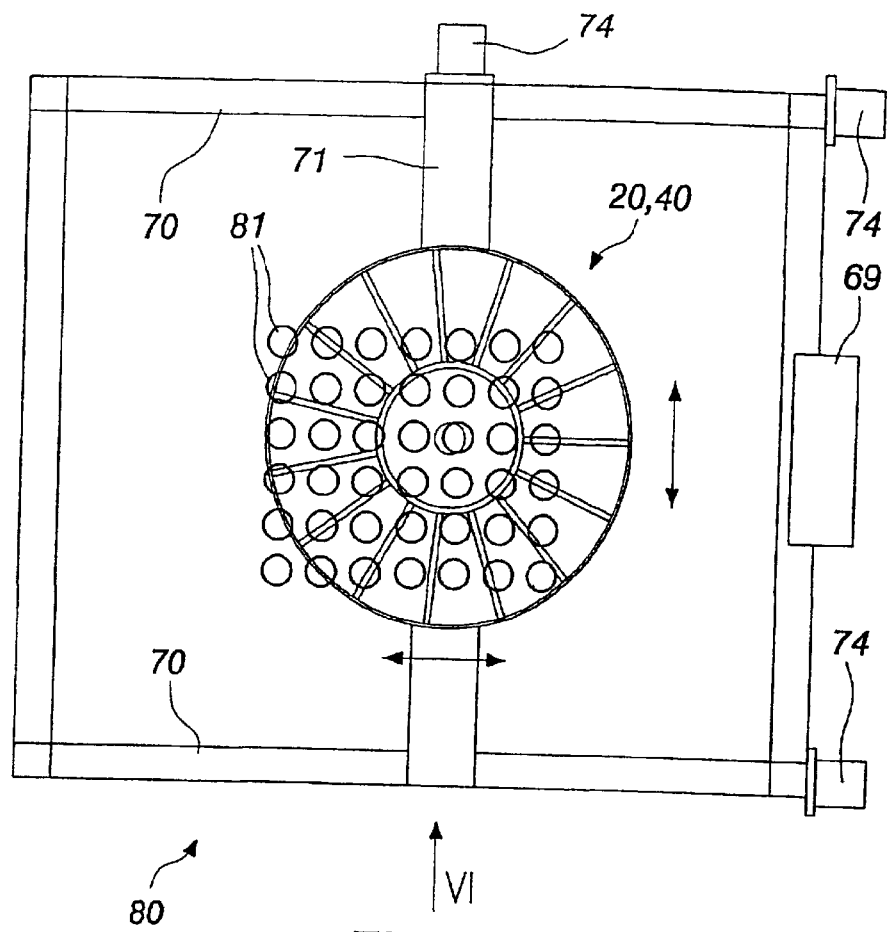
FIG. 5 shows in a plan view an automatic loading and medicine selection device for loading dosage cartridges.
Figure 6:
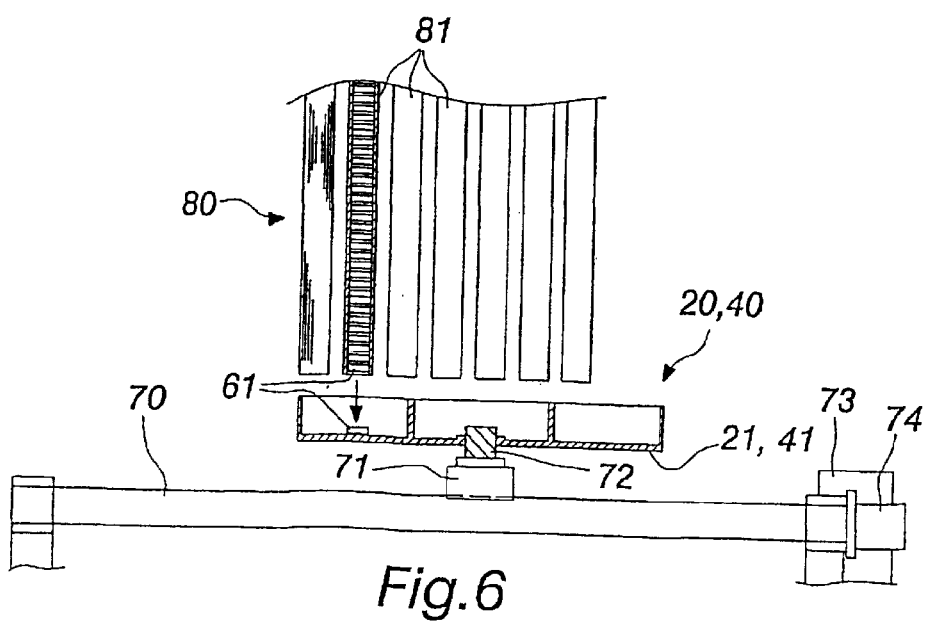
FIG. 6 shows the loading device in a side view.

FIGS. 5 and 6 depict a loading device 80 for filling the dosage compartments 27, 47 of the cartridges 20, 30 and 40, 50 with selected medicines according to prescription.

The loading device 80 is programmed for loading or dosing selected medications prescribed by a physician in any of the cartridges. The cartridges are interchangeable and designated or re-designated for a certain user after each filling. The loading device 80 is made up by a plurality of tubular medication feeders 81 set in a plurality of rows. The loading device 80 according to the present embodiment has its feeders 81 arranged in six rows, each row comprising seven feeders 81, i.e. the loading device 80 consisting of 42 feeders 81. Each feeder 81 is used for supplying a single type of pill- or capsule-form medication 61. The operating principles of such feeders are prior known technology for a skilled person and, thus, not described in more detail in this context.

Figure 8:
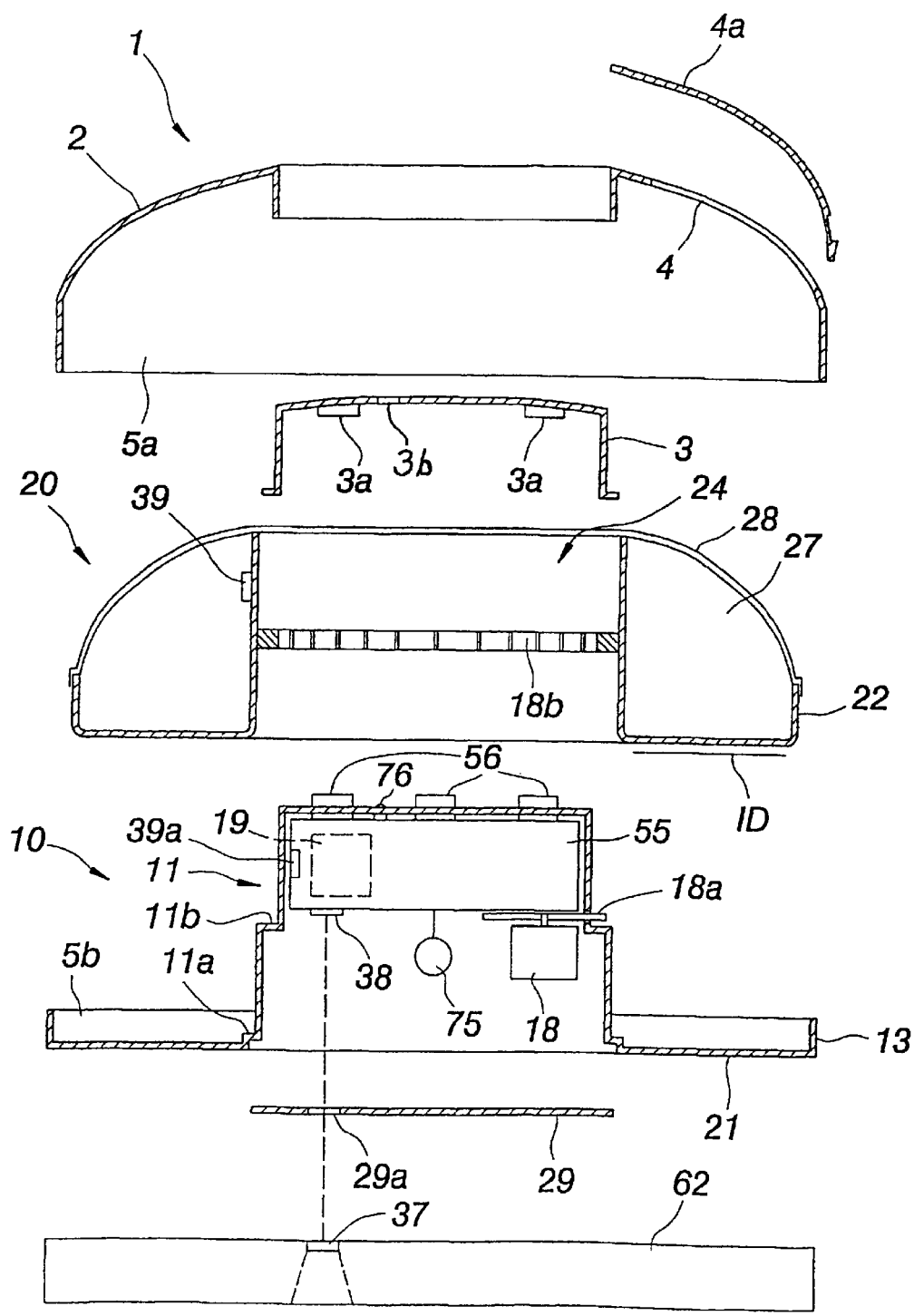
FIG. 8 shows schematically a medication dispenser according to a second embodiment useful as part of a system of the invention.
Figure 9:
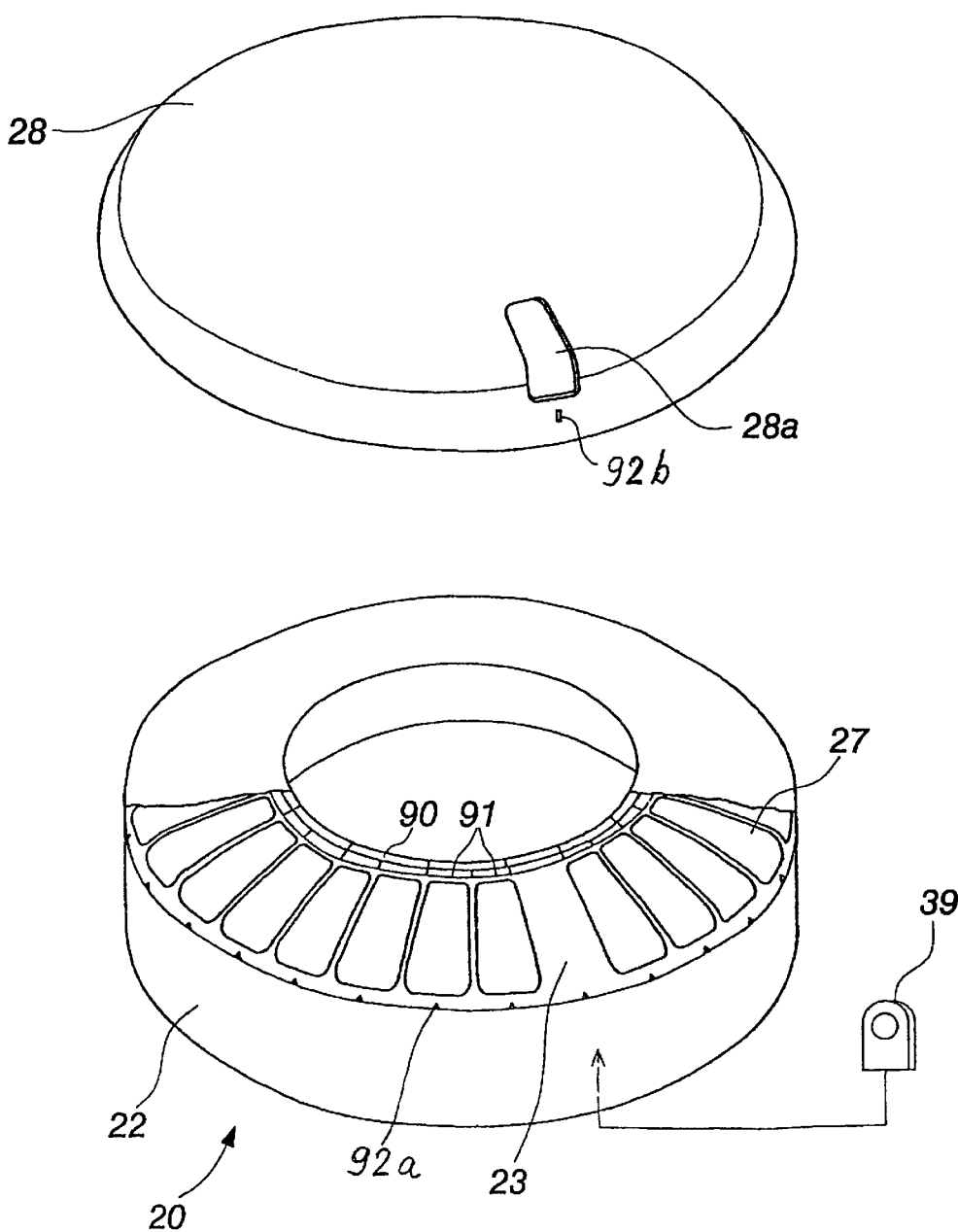
FIG. 9 shows a dosage cartridge for the dispenser of FIG. 8.

The cartridge 20, 40 according to embodiment of FIGS. 1–4 is set for a planar movement underneath the dosage feeder 81 in a position upside down (relative to operating position in dispenser) and without the base disc 30, 50. The cartridge 20 according to embodiment of FIGS. 8 and 9 is set in a position which is also the operating position in dispenser. The cartridge is preferably secured by the central hole 24, 44 to a clamp 72 movable along guides 70, 71 or the like. Motors 74, driven according to a loading program, are used for shifting each dosage compartment 27, 47 in turn and in compliance with a preset program underneath a desired feeder 81, wherefrom a desired medication 60 can be delivered into the appropriate dosage compartment 27, 47. The cartridge 20, 40 may of course be also adapted to be rotated by the clamp 72 and the feeders 81 may be arranged in a circle or successively in a single row or in some other preferred pattern.

To the top cartridge surface 21, 41, which functions as the bottom surface as a cartridge is filled, (or to the bottom surface of cartridge in FIGS. 8 and 9) is attached an identification label ID by a mechanism 73 associated with the loading device 80, on the basis of which information the filled cartridge 20 can be certifiably returned to a proper dispensing device.

Figure 7:
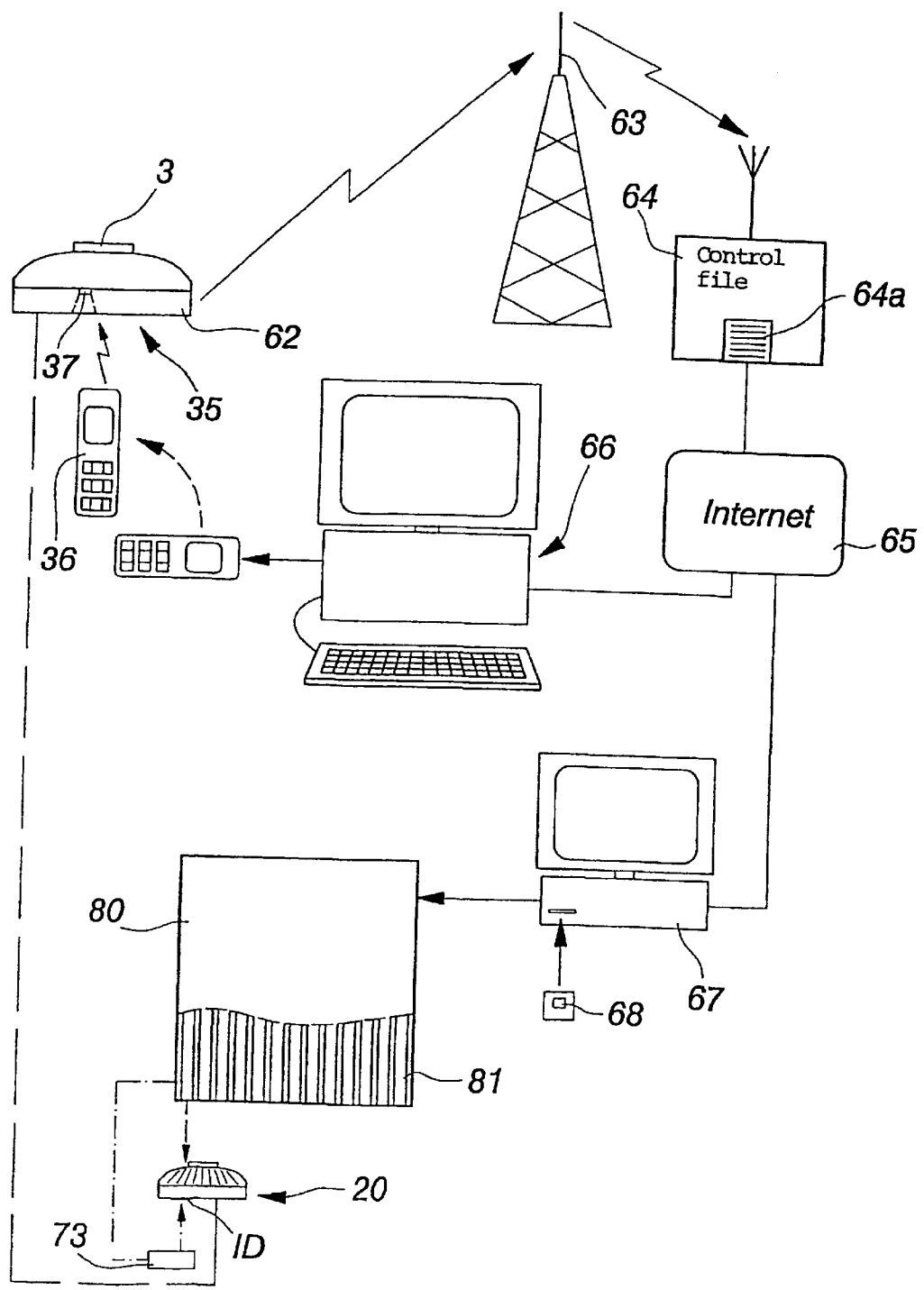
FIG. 7 shows a block diagram for a system of the invention.

The following description deals with a system of the invention with reference to FIG. 7. A dispensing device 35 may be like the one described above or to be described subsequently with reference to FIGS. 8 and 9. The dispensing device 35 is fitted with a radio transmitter, such as a GSM module 62, which is adapted to automatically transmit information regarding dispensing events by way of a wireless communication link 63 to a predetermined control file 64a, which is included e.g. in a server 64 of a wireless communication or internet service provider (operator). The control file thus includes a dispensing event log which can be checked in real time with the progress of dispensing via internet by any person having the necessary code key. The operator's server 64 can further include a program for automatic control of the dispensing event log and for giving an alarm to one or more predetermined caregiver, nurse or doctor if a predetermined number of dispensing events have failed. The control file 64a may also be included in the bulk storage of a facility computer 66 in a hospital or an agency responsible for home health care. Said computer 66 as well as the server 64 are in mutual communication by way of an internet link 65. Thus, the control file 64a can be monitored by way of the internet from any computer, as long as a password linked with the control file 64a is known. This substantially reduces unnecessary visits for checking the dispersing events. Furthermore, this advantage is achieved without particular intelligence in the dispenser.

The prescription controlling the loading device 80 in terms of its filling action is adapted to be delivered, along with a patient's identification data, by way of a communication network, such as the internet 65 or a chip card 68, to a computer 67 controlling operation of the loading device 80. Alternatively, the prescription can be delivered conventionally on a paper printout, from which the necessary information is transferred by typing to the computer 67 controlling the dosage.

The cartridges 20, 40 are adapted to be disengaged from the dispensing device 35 and to be transferred to the loading device 80 for filling or loading the dosage compartments 27, 47 of a cartridge with desired doses of medication. In addition, the mechanism 73 associated with the loading device 80 furnishes the loaded cartridge 20 with identification data ID, on the basis of which the loaded or filled cartridge 20, 40 can be certifiably returned to the correct dispensing device 35.

Figure 10:
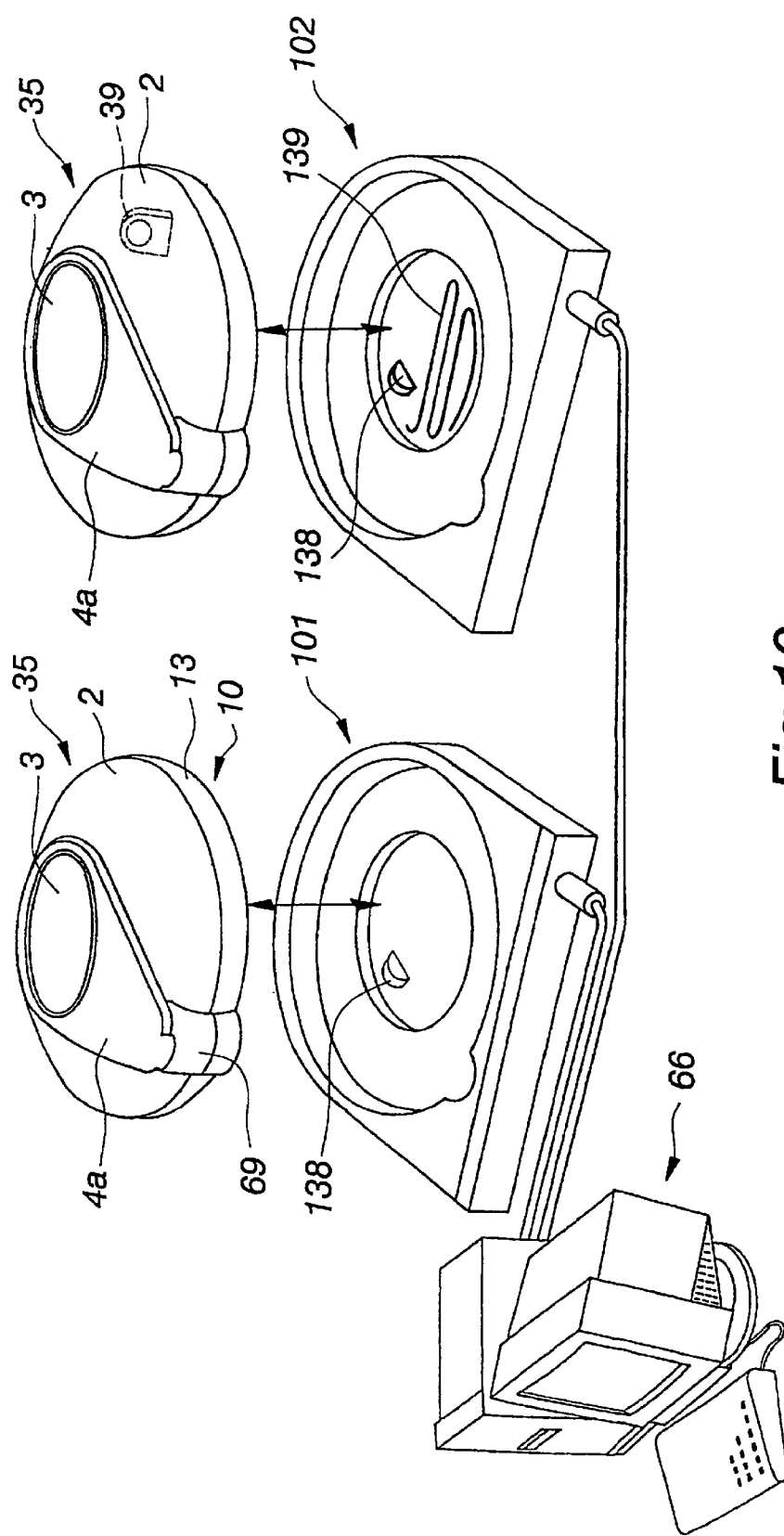

The dispensing device 35 has its program electronics 19 reprogrammable with an external programming unit. In the depicted case, the external programming unit comprises a mobile telephone 36, whereby a dispensing program or its updatings can be fed to the program electronics 19 by way of an IR link 37, 38 shown in FIG. 8. The external programming unit for a dispensing program may also comprise the facility computer 66, which has a communication via the internet 65 with the control file 64a or which has the control file stored in its bulk memory. In the latter case, the dispensing device 35 can be brought to the IR link 138 (shown in FIG. 10) of the computer 66 for programming or the program can be transferred from the computer 66 to the mobile phone 36, whereby the program is delivered further to the program memory 19 of the dispensing device 62.

The cartridge 20, 40 can be furnished with identification data, e.g. by attaching to the cartridge an identification-data carrying label ID by means of the mechanism 73. Optionally or additionally, the identification can be certified according to the embodiment shown in FIGS. 8 and 9 by providing the cartridge 20 with an electronic identification tag 39, which the loading device 80 furnishes with identification data and information of prescribed medicines and of dispensing program for a given customer. Such data may include e.g. a patient, a hospital, medications, and a physician. The dispensing device has its housing 10 provided with elements 39a for reading the information disclosed in the identification tag 39. Since reading elements are comparatively expensive, it is preferable that in hospital environment be employed a separate reading device 102 (FIG. 10), which is located e.g. in a nurses' station and which has an antenna 139 for reading the RF-tag 39 and an IR link 138 for delivering the read-out information to a dispensing device. Upon the arrival of dosage cartridges 20 filled with doses of medication, a nurse proceeds to pick up respective dispensing devices from patients' rooms and to transfer the tag-disclosed information by way of a reading device 102/139 and an IR link 138 to the memory 19 of a dispensing device 20. Before such reading and transferring, a matching cartridge has been inserted in a proper dispensing device.

The following description deals in even more detail with the dispensing device shown in FIG. 8. The dispensing device is provided with a cover or housing 1, comprising a shell portion 2 which includes a dispensing outlet 4 and a flap 4a for closing the same, if necessary. The components 2 and 4a can be manufactured in moulded plastics and at least the flap 4a is transparent (shell portion 2 may be non-transparent). The flap 4a may have its base hinged in such a way that the flap 4a can be removed as required, if a patient finds it difficult to operate a locking mechanism attached to its outer end. A push button 3 fits in a central hole in the shell portion 2 and is manufactured from transparent stained plastics. The colour of the push button 3 can also be used for encoding a loading device. The push button 3 is provided with a transparent window (not shown) for monitoring a timer display (the window can be covered as required). In addition, the push button 3 is provided with an opening 3b for a led light indicator 76.

The cartridge 20 comprises preferably a transparent machine-washable plastic manufactured in food-grade plastics. The cartridge is provided with 28 dosage compartments 27 for tablets. The cartridges 20 are interchangeable between various dispensing devices. The cartridge has its central hole 24 provided with a gear rim 18b, which supplies the cartridge with its rotary drive from a gearwheel 18a of the motor 18 placed in the central hollow of the housing 10 (the necessary gear between the motor 18 and the gearwheel 18a has not been shown).

The housing 10 is manufactured in transparent plastics e.g. as a plastic extrudate. Consequently, a prescription or an identification tag ID, attached to the bottom of the cartridge 20, is visible as required through a transparent floor 21 of the housing 10. Through a rim collar 13 of the housing it is possible to visually observe medications remaining in the dosage compartments 27 of a cartridge (even in the case that the shell portion is non-transparent).

An electronics unit 55 is disposed inside a cylindrical central hollow 11 within the housing 10. The electronics unit is provided with a memory-equipped, programmable processor 19, which can be programmed with four daily times for medication by means of key buttons 56 or an IR link 37, 38 included in the unit 55. In addition, the program takes care of necessary safety times and delay times, as well as a deadline for the ingestion of a dose. The IR link 37, 38, included in the unit 55, along with the GSM module 62, serving as an accessory, enables a telecontrol over medication and eventual alarms regarding malfunctions, as described in conjunction with FIG. 7. Hence, the program takes care of the specification-compliant function of a dispensing device and, merely by modifying the program, it is possible to develop various versions of a dispensing device. Naturally, the IR link can be replaced with an RF link or other links operating in compliance with standards.

A floor panel 29, having a hole 29a for the operation of an IR link, encloses the housing hollow 11 which has space also for a sound signal device 75 and a battery.

The motor 18 comprises e.g. a stepped motor, which activates its operation upon pressing down the push button 3 as pins 3a depress the programming keys 56 of the electronics unit 55. However, this activation only occurs after the signaling device 75, 76 has been activated under the control of program electronics 19, 55. Every time the elements 18, 18a operating the cartridge 20 are activated, the information about a dispensing occurrence is transmitted to the control file 64a mentioned in connection with FIG. 7, which comprises e.g. a www-page in the internet and which constitutes a monitoring log for taking the medication. Optionally, a memory associated with the program electronics 19, 55 is used to collect information about dispensing occurrences and to transmit the same at prescribed times to said control file 64a.

Thus, the electronics unit 55 included in the dispensing device is programmable either by a patient him- or herself or by medical personnel (keys 56) or by means of the computer 66 or utilizing an IR link 138 in the programming device 101 or 102, or in the GSM telephone 36. According to its programming, the dosage dispenser electronics 19, 55, 75, 76 outputs a signal to the user whenever it is time for medication and prevents the ingestion of any dose of medication other than the one to be taken at that precise time.

As the dosage cartridges 20 containing doses of medication are carried independently of a dispensing device from the loading device 80 to the dispensing device 35, the dosage cartridge 20 must be provided with a cover 28. This cover 20 may be a rotatable cover of thin transparent plastics, which is provided by a loading opening 28a (FIG. 9) for manual loading. The cover 28 is removed as the cartridge 20 is inserted in the housing 10. The cover 28 may also remain attached to the cartridge 20 included in a dispensing device, in which case the cover 28 must be provided with a respective central hole 24 and the cover 28 must be rotatable relative to the cartridge 20, such that the hole 28a present in the cover 28 always remains in line with the outlet 4 of the shell portion 2 while the cartridge 20 is rotating. The cartridge turns an angular distance equal to the dosage compartment 27 every time the push button 3 is depressed at the accepted medication time. The stepped motor 18 can be used for the precise determination of an angle of rotation in such a way that, even after quite a long-term use, the dosage compartments 27 always coincide with the dispensing outlet 4.

As shown in FIG. 9, mechanical detents 92a around the periphery of the cartridge 20 can be used to fit with a complementary detent 92b in the cover 28 to slightly hold the rotation of the cover 28 each time the opening 28a coincides with the dosage compartment 27.

FIG. 9 illustrates a section from the rim of a cartridge (the rest of the rim being also provided by compartments 27 though not shown). The dosage compartments 27 are narrow and high so as to accommodate 28 of those along a relatively small circular arc. This configuration is beneficial in terms of both elongated capsules and circular pills. Between the dosage compartments 27 is a vacant recess or space 23 and in line therewith the dispenser bottom 10/21 is provided with a protrusion (not shown), which is insertable in the space 23 (from the bottom side thereof) as an indication for inserting the cartridge 20 in the housing 10 of the dispensing device 35 (and similarly in the loading device 80) in a preset initial position. The cartridge 20 rests upon setbacks 11b and 11a included in the cylindrical housing hollow 11. Space 23 can be utilized also for receiving the RF-tag 39.

The jacket or shell portion 2 has a bottom edge which can be locked with an appropriate forming to the top edge of an outer housing rim 13. In view of switching the cartridges 20, there must be an engagement between the jacket 2 and the housing 10 which is readily disconnectable and reconnectable (if necessary, also lockable). This can be implemented e.g. by forming the opposing edges with a combination of short threading and bayonet coupling. A lock cylinder may be placed inside the protrusion 69.

As shown in FIG. 9, there is a schedule ring 90, 91 close to the inner rim of the openings of the dosage compartments 27. This schedule ring is a replaceable paper or plastic ring having a first ring divided into sections 90, each section 90 corresponding to a certain day of a week typed in the corresponding section 90. Such a "week day section" covers 1–4 compartments 27. A second ring is divided into subsections 91 of the "week day sections" 90, indicating first, second etc. medicine of a day. With this kind of scheduling ring and the rotatable cover 28 with opening 28a, the cartridge can also be used as a manually operated dispensing cartridge also without the actual dispensing device. This is a clear benefit of the cartridge construction, which facilitates the manual loading in one hand, but enables automated loading on the other hand, and is furthermore applicable to be used with or without the intelligent dispensing device.

Figure 11:
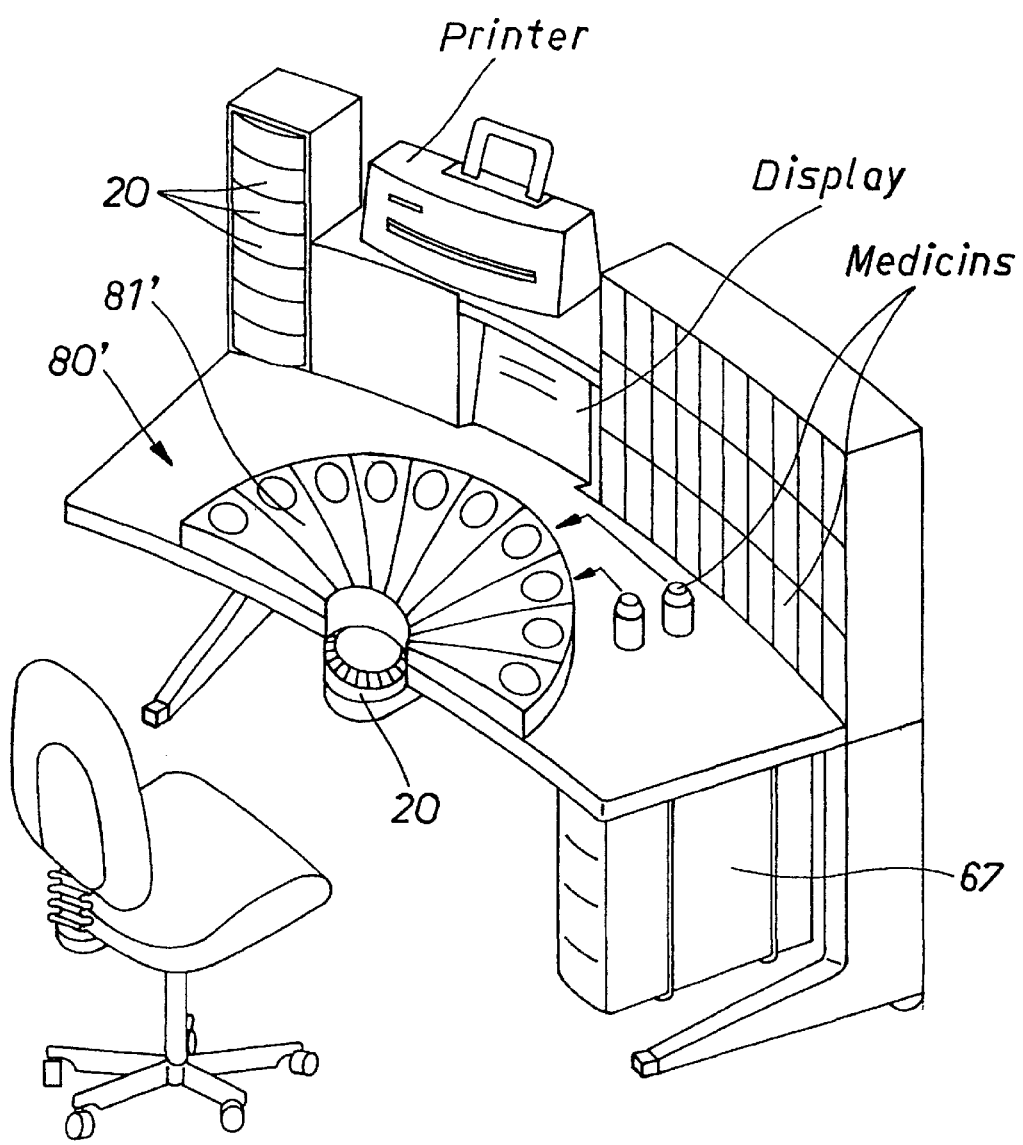
FIG. 11 illustrates a schema of an alternative loading device located for example in a dispensary or druggist's.

FIG. 11 shows a semi-automatic loading device 80' having feeders 81' arranged in a semi circle from medicine receptacles to the periphery of cartridge 20 which is rotated automatically under control of the computer 67 and the prescription fed in the computer 67. The cartridges 20 are manually changed and the medicine receptacles are manually filled. Also in this case it is important to provide each and every cartridge 20 with the identification label ID and/or with the RF-tag bearing the identification information. Preferably, at least an optically readable ID label is attached to the cartridge by means of the loading device 80, 80'.

As can be learned from the above description the invention serves an advanced logistics for delivering medicines from dispensary to the users (patients) and for efficient monitoring of appropriate use or disposition of the medicines.

What is claimed is:

1. A system for dispensing pill- or capsule-form medications (61) in desired doses (60), said system comprising a dispensing device (35) which includes a housing or frame (10), a cartridge (20, 40) rotatably supported on the housing or frame (10) and provided with individual dosage compartments (27, 47) for desired doses of medication, the cartridge (20, 40) being adapted to be disengageable and removable from the dispensing device (35) for filling the dosage compartments (27, 47) of the cartridge with desired doses of medication, the cartridge being furnished with identification data (ID), on the basis of which the filled cartridge (20, 40) can be certifiably returned to the proper dispensing device (35), a signaling device (75, 76) giving a sound and/or light signal, which activates at pre-programmed points of time, and an electronics unit (19, 55) containing a dispensing program, the program electronics (19) being re-programmable with a programming device (55, 56; 36, 66, 101, 102) and that the dispensing is arranged to be effected by means of the users own action which is exerted onto the dispensing device (35), characterized in that the users own action for dispensing rotates or controls, rotation of the cartridge (20, 40) to bring an individual dosage compartment (27, 47) into a dispensing position, and that the said users own action for dispensing, or lack of such action within a prescribed time, is adapted to automatically transmit information regarding the dispensing event by way of a communication link (62, 63) to a distant control file (64a), which can be accessed and monitored by persons having a correct key code or password.

2. A system as set forth in claim 1, characterized in that the cartridge (20) is furnished with a rotatable and removable cover (28) having an opening (28a) which can be rotated to coincide with any of the dosage compartments (27) for loading and/or dispensing of doses through the opening (28a), and that the cartridge is further provided by means (90, 91) for visual indication of dispensing schedule.

3. A system as set forth in claim 1, characterized in that the system includes a separate dosing or loading device (80, 80') for filling the dosage compartments (27, 47) of the cartridge with desired doses of medication and for furnishing the filled cartridge (20, 40) with identification data (ID).

4. A system as set forth in claim 1, characterized in that the programming device (36, 66, 101, 102) is an external portable device, which has a wireless communication link (37, 138) with the electronics unit (19, 55) of the dispensing device (35).

5. A system as set forth in claim 3, characterized in that the prescription controlling the loading device (80) in terms of its filling action is adapted to be delivered, along with a patient's identification data, by way of a communication network, such as the internet or a chip card (68), to a computer (67) controlling operation of the loading device (80).

6. A system as set forth in claim 1, characterized in that the dispensing device (35) is provided with a transmitter, such as a GSM module (62), which is adapted to transmit automatically information regarding dispensing occurrences by way of a communication link (63) to a predetermined control file (64a) at a distant control terminal (64, 66), which is provided by a program for monitoring the dispensing events saved in the control file (64a).

7. A system as set forth in claim 1, characterized in that the control file (64a) is linked to the internet (65) in such a way that the control file (64a) can be monitored via the internet, as long as a password associated with the control file (64a) is known.

8. A system as set forth in claim 4, characterized in that the external programming device (36, 66, 101, 102) for a dispensing program comprises either a mobile telephone (36) or a programming device (101, 102) equipped with an IR link (37, 38, 138) for feeding the dispensing program, or modifications thereto to the electronics unit (19, 55).

9. A system as set forth in claim 4, characterized in that the external programming device (36, 66, 101, 102) for a dispensing program comprises a computer (66), which has a link via the internet (65) to the control file (64a) or which has the control file stored in its bulk memory.

10. A system as set forth in claim 3, characterized in that the loading device (80, 80') is adapted to provide the cartridge (20, 40) with an optically readable label (ID) disclosing the identification data.

11. A system as set forth in claim 3, characterized in that the cartridge (20) carries an electronic identification tag (39), which the loading device (80, 80') furnishes with identification data for a customer, and that the dispensing device (35) or a hospital dispensary is provided with elements (39a; 102/139) for reading the data disclosed in the identification tag (39).

12. A system as set forth in claim 1, characterized in that the means (18, 18a) for manipulating the cartridge (20) are activated to function upon pressing a push button (3), but only after the signalling device (75, 76) has activated under control of the program of the electronics unit (19, 55).

13. A system as set forth in claim 1, characterized in that, upon every activation of the means (18, 18a) manipulating the cartridge (20), the information about a dispensing occurrence is transmitted to said control file (64a), which compiles a monitoring log of taking a medication.

14. A system as set forth in claim 1, characterized in that the electronics unit (19, 55) involves a memory which collects information regarding dispensing occurrences and transmits the same at prescribed times to said control file (64a), which compiles a monitoring log of taking a medication, the prescribed times being short enough for practically real time monitoring of taking a medication.

15. A system as set forth in claim 1, characterized in that the electronics unit (19, 55) containing a dispensing program is programmable by means of push buttons (56) included therein.

16. A system as set forth in claim 1, characterized in that between the dosage compartments (27) of the cartridge (20) is a vacant recess or space (23) and the housing or frame (10) of the dispensing device is provided with a protrusion, which functions as a response and/or an indication for inserting the cartridge (20) in the housing or frame (10) of a dispensing device in a preset initial position.

17. A system as set forth in claim 1, characterized in that the cartridge (20, 30 and 40, 50) includes a substantially circular base disc (30, 50), having radially inbound elongated cuts or slits (34, 54) provide its outer periphery with sector-shaped flexible flaps (31, 51) which constitute a floor for the dosage compartment (27, 47), and that in the vicinity of the dispensing point (12) are provided manually operated bending means (3, 7, 8a, 9a) for deflecting the flap (31, 51) to extend obliquely downwards from the plane of the base disc (30, 50) and for releasing the dose of medication (60) from the dosage compartment (27, 47).

18. A system as set forth in claim 1, characterized in that at least one cartridge (20, 40) is encloseable within a space (5) defined by a cover (2) mountable around the frame (10) and the cartridge (20, 30 and 40, 50).

19. A system as set forth in claim 18, characterized in that the cover (2) is lockable securely to the frame (10) by means of a common locking mechanism (16, 17; 69) between the cover (2) and the rim portion (13) of the frame (10).

20. A system as set forth in claim 1, characterized in that a stepping motor (18) rotates the cartridge (20, 30 and 40, 50) in compliance with a program programmed in a programmable memory of the electronics unit (19, 55).

21. A system as set forth in claim 1, characterized in that, with the base disc (30, 50) or the removable cover (28) set in its position, the dosage compartments (27, 47) are closed on all sides thereof.

22. A system as set forth in claim 1, characterized in that, the cartridges (20, 40) are made of transparent plastics and also the dispensing device is partially made of transparent plastics to allow visual inspection of the doses in the dosage compartments.

23. A system as set forth in claim 12, characterized in that a stepping motor (18) rotates the cartridge (20) through an angular distance equal to the dosage compartment (27) as the dispensing button (20) is pressed at the accepted medication time, which is programmed in the program of the electronics unit (19, 55).

* * * * *